(12) United States Patent
Voges et al.

(10) Patent No.: US 6,348,046 B2
(45) Date of Patent: *Feb. 19, 2002

(54) URINE MEASURING DEVICE

(75) Inventors: Karl-Friedrich Voges; Martin Sippel, both of Melsungen (DE); Rémi Collin, Epernon (FR)

(73) Assignee: B. Braun Melsungen AG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/432,227

(22) Filed: Nov. 3, 1999

(30) Foreign Application Priority Data

Nov. 17, 1998 (DE) ..................... 298 20 526 U

(51) Int. Cl.[7] .................................................. A61M 1/00
(52) U.S. Cl. ..................................................... 604/323
(58) Field of Search ................................. 604/317, 318, 604/322, 323, 324, 325, 326, 335, 544; 220/4.06, 4.21, 4.24, 4.26, 501, 203.03

(56) References Cited

U.S. PATENT DOCUMENTS

| | | | | |
|---|---|---|---|---|
| 3,583,401 A | * | 6/1971 | Vaillancourt | |
| 3,604,420 A | * | 9/1971 | Vaillancourt | |
| 3,831,453 A | * | 8/1974 | McWhorter | |
| 3,965,900 A | | 6/1976 | Boedecker | |
| 3,968,925 A | * | 7/1976 | Johnston et al. | |
| 4,158,362 A | * | 6/1979 | Durrent et al. | |
| 4,334,537 A | | 6/1982 | Peterson | |
| 4,354,492 A | * | 10/1982 | McPhee | |
| 4,490,144 A | * | 12/1984 | Steigerwald | |
| 4,615,693 A | * | 10/1986 | Paradis et al. | |
| 4,629,159 A | * | 12/1986 | Wellenstam | ............. 251/149.6 |
| 4,743,236 A | * | 5/1988 | Manschot | |
| 6,254,581 B1 | * | 7/2001 | Scott | ......................... 604/317 |

FOREIGN PATENT DOCUMENTS

DE        4137074        11/1991

* cited by examiner

Primary Examiner—Sharon Kennedy
Assistant Examiner—Catherine Serke
(74) Attorney, Agent, or Firm—Diller, Ramik & Wight

(57) ABSTRACT

The urine measuring device comprises at the lower end of a drip chamber (15) an antireflux valve which prevents liquid from a measuring chamber (11) from refluxing into the drip chamber (15). A valve plate (30) capable of closing the valve opening (26) comprises a loose part which is loosely arranged in the valve chamber (34) and rests on a bracket (28) when the urine measuring device is in upright position. If the urine measuring device is tilted, the urine contained in the measuring chamber (11) presses the valve plate (30) against the valve seat (27) so that reflux into the drip chamber (15) is prevented.

13 Claims, 3 Drawing Sheets

URINE MEASURING DEVICE

BACKGROUND OF THE INVENTION

The invention relates to a urine measuring device and in particular to a urine measuring device comprising a drip chamber with an antireflux valve.

Urine measuring devices serve for collection of the urine leaving the patient's body through a catheter. Germs from the environment may enter the measuring container of the urine measuring device and grow there. Such germs may enter the patient's body via the connecting tube leading to the patient's body and cause infection of the urinary passages. To prevent such infections urine measuring devices are generally provided with a Pasteur chamber at the place where the connecting tube leads into the measuring container. Said chamber comprises a drip chamber with a dropper on the supply side and an antireflux valve on the discharge side. In the drip chamber the liquid column coming from the connecting tube is stopped. The urine drops from a dropper tip and falls freely through the air without wetting the walls of the drip chamber. The germs are not capable of moving along the dry walls towards the patient's body.

During a collecting phase (normally one hour) the urine measuring device is suspended vertically on the patient's bed. At the end of the collecting phase the quantity of urine is recorded and the measuring container is discharged into the urine bag. For this purpose the measuring container is tilted by more than 90°. It would be possible that the refluxing urine wets the dropper and the inner walls of the drip chamber so that the germ barrier would be overcome. To prevent this it is common practice to provide an antireflux valve on the bottom of the drip chamber.

An antireflux valve in conjunction with said drip chamber is described in U.S. Pat. No. 3,965,900. Said antiflux valve comprises a valve flap closing a lateral opening of the drip chamber with the valve flap being biased into the closing position by a holding element. The holding element and the valve flap form a check valve. Said check valve comprises at least two parts of which the holding element has a complex form. Therefore the manufacture involves relatively high costs and efforts.

An antireflux valve is described in U.S. Pat. No. 4,334,537. Said antireflux valve comprises a valve chamber with a valve seat against which a valve disk is drawn. The valve disk is formed integral with a holding rod provided with spring-type anchoring elements at its ends. The manufacture of such a complex valve body involves considerable costs and efforts.

Further, it must be taken into consideration that together with the urine solids (blood clot, gravel) may be transported which deposit in the valve and keep it open.

A urine measuring device in which a check valve is provided at the lower end of the measuring chamber is described in German Patent Publication 41 37 074 A1. The check valve comprises a valve plate which presses against a circumferential valve seat arranged on the bottom side of the valve opening. No information is furnished on the valve plate fastener and the valve plate operation.

SUMMARY OF THE INVENTION

The object of the invention is to provide a urine measuring device comprising a drip chamber and an antireflux valve, which precludes the danger of malfunction caused by solids and which can be manufactured and assembled is an easy and inexpensive way.

The invention is based on the idea that the valve must generally be open but on the other hand be closed tight in the closing position. Further, the valve should be amply dimensioned to prevent deposition of blood clots or gravel. According to the invention the urine measuring device is provided with a valve plate comprising a freely movable loose part. This means that the valve plate is not permanently fixed to any place or any other part but is rather a freely movable part. The valve plate is a flat plate which does not comprise any shoulders etc. projecting from the plate plane. The valve plate fits from below closely to a valve seat when an external force exerted by the reflux liquid acts upon it. In the unloaded condition the valve plate is located apart from the valve seat so that valve opening is open. This means that the dripping urine can pass by gravity through the valve opening. If the urine measuring device is tilted for the purpose of discharging the measuring chamber or for any other reason, the urine contained in the measuring container presses the valve plate against valve seat thus sealing the latter. This prevents refluxing urine from entering the drip chamber and wetting its walls. Since the walls of the drip chamber remain dry, they do not form any bridges which allow germs to travel towards the patient's body.

An essential advantage of the invention is that the valve is integrated in the measuring device housing and requires the valve plate as the only specific additional part. The parts of the valve housing may be integrated in the measuring device housing as a single unit so that separate manufacture or assembly is not necessary. The valve plate is a flat plate which requires no particular three-dimensional forming. It can rather be punched out of a suitable flat sheet material, preferably polyester sheet. The valve plate is relatively stiff and dimensionally stable and is preferably made of semirigid plastic material.

The valve plate is loosely supported between lateral guide elements. This means that the valve plate is at no place permanently fixed to the valve housing. The guide elements form a kind of cage in which the valve plate is movable. They are arranged in such a way that in each possible position the projection of the valve plate completely covers the valve opening.

The lateral guide elements are preferably made of ribs which extend inwardly from the valve housing wall with the valve housing having a larger cross-section than the valve opening.

Thus a large passage cross-section is available. Due to the absence of elastic tensioning means and due to a large free passage cross-section there is no danger that solid matter contained in the urine affect the functioning of the valve.

According to a further aspect of the invention the valve, except for the valve plate, forms an integral part of a measuring device housing containing the drip chamber. Here, no additional components need be incorporated in the housing during assembly. The valve plate is merely inserted into the cavity provided for this purpose without any fixing being required.

According to a preferred embodiment of the invention the measuring device housing comprises two housing parts which are attached to each other. The valve opening and the guide elements are components of the one housing part and a bracket supporting the valve plate is a components of the other housing part. For assembly purposes merely the two housing parts are attached to each other with the valve plate being interposed.

The cross-sectional area of the valve opening is preferably at least 70% larger than the internal cross-section of the dropper. This ensures an adequate dimension of the valve opening so as to prevent clogging.

BRIEF DESCRIPTION OF THE DRAWINGS

Hereunder an embodiment of the invention is explained in detail with reference to the drawings in which.

DESCRIPTION OF THE PREFERRED EMBODIMENT

Figure 1:
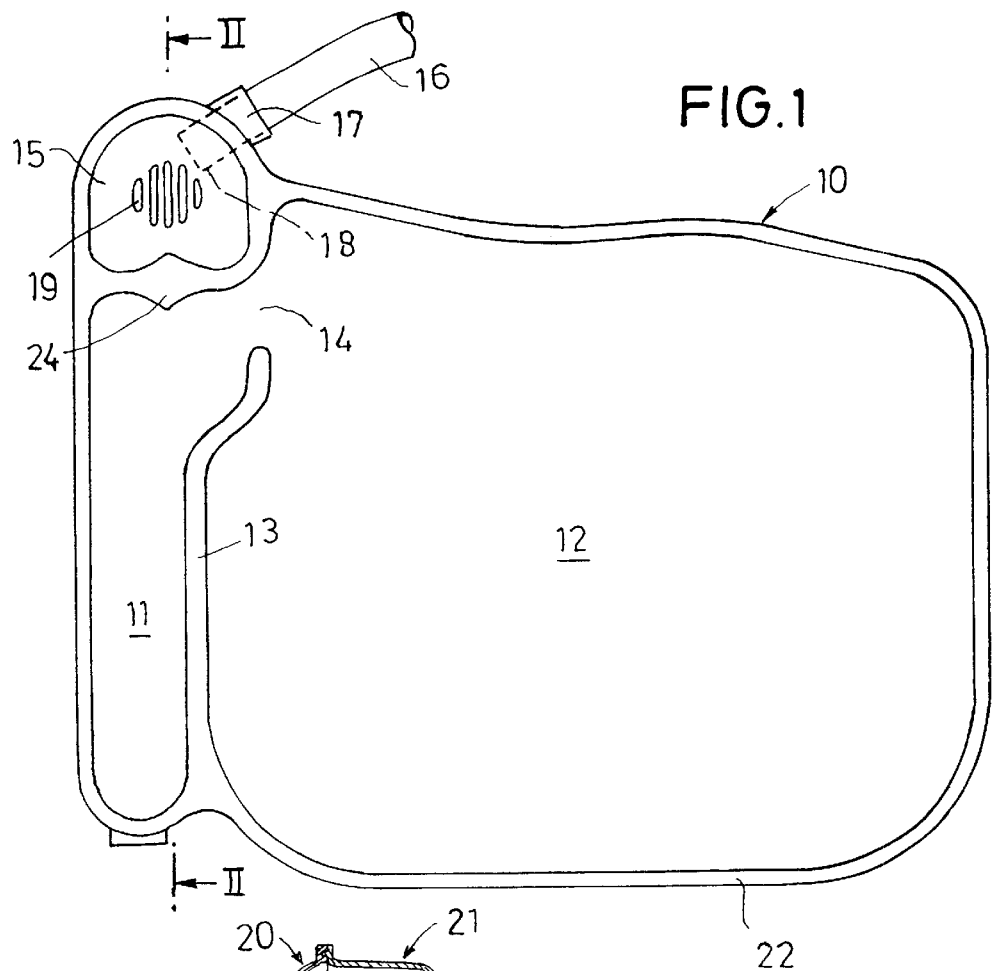
FIG. 1 shows a front view of the urine measuring device.
Figure 2:
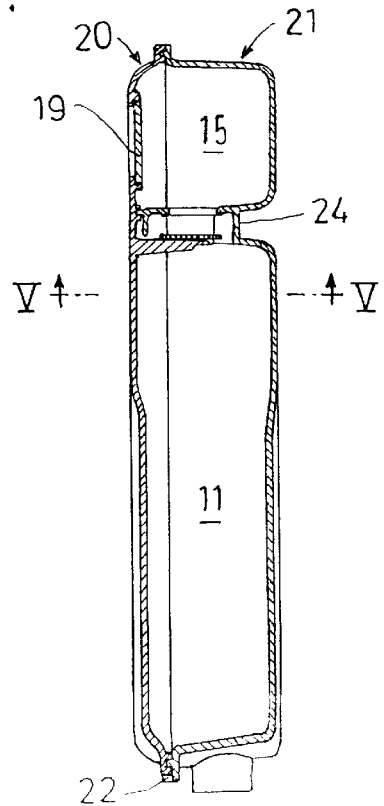
FIG. 2 shows a section along line II—II of FIG. 1.

The urine measuring device comprises a measuring container 10 made up of a fine measuring chamber 11 and a coarse measuring chamber 12. The fine measuring chamber and the coarse measuring chamber are separated from each other by a web 13 and connected to each other by an overflow 14 arranged at the upper end of the web 13.

Above the fine measuring chamber 11 a drip chamber 15 is located into which leads a supply tube 16 coming from the patient's body. The supply tube 16 is attached to a tube fastener 17. The supply tube is glued in place in such a way that a length of some millimeters of its front end extends into the drip chamber 15 and forms a dropper 18. At the front side of the drip chamber 15 a venting filter 19 is attached which communicates with the ambient air.

The drip chamber 15, the fine measuring chamber 11 and the coarse measuring chamber 12 are components of a measuring device housing comprising two housing parts. The one housing part 20 forms the front part and the other housing part 21 forms the rear part. Front part and rear part are glued or welded to each other via a circumferential groove-and-tongue-connection 22. The groove-and-tongue-connection 22 extends around the entire measuring device housing and along the internal walls.

In the transition area between drip chamber 15 and fine measuring chamber 11 the valve housing 24 is configured. Said valve housing comprises the components of the two housing parts 20, 21 attached to each other and forming single-piece shaped plastic parts.

The valve housing 24 comprises a horizontal partition wall 25 forming the bottom wall of the drip chamber 15. In the transition wall 25 the circular valve opening 26 is provided. The lower edge of the valve opening 26 forms the collar-shaped circumferential valve seat 27.

A bracket 28 is arranged at a distance below the valve opening 26, which projects inwardly from the front wall 29 pertaining to the housing part 20 and extends approximately in parallel to the partition wall 25. Said bracket forms a supporting surface or receiving surface for the valve plate 30.

The valve plate 30 is made of a plastic sheet material, preferably polyester sheet. Its specific gravity is larger than that of urine. Said valve plate is a punched-out round plate which is loosely inserted into the valve housing 24. The valve plate 30 is retained in a central position by lateral guide elements 31 in the form of ribs which project inwardly from the wall of the valve housing 24. The guide elements 31 are, together with the partition wall 25, components of the rear housing part 21.

Figure 5:
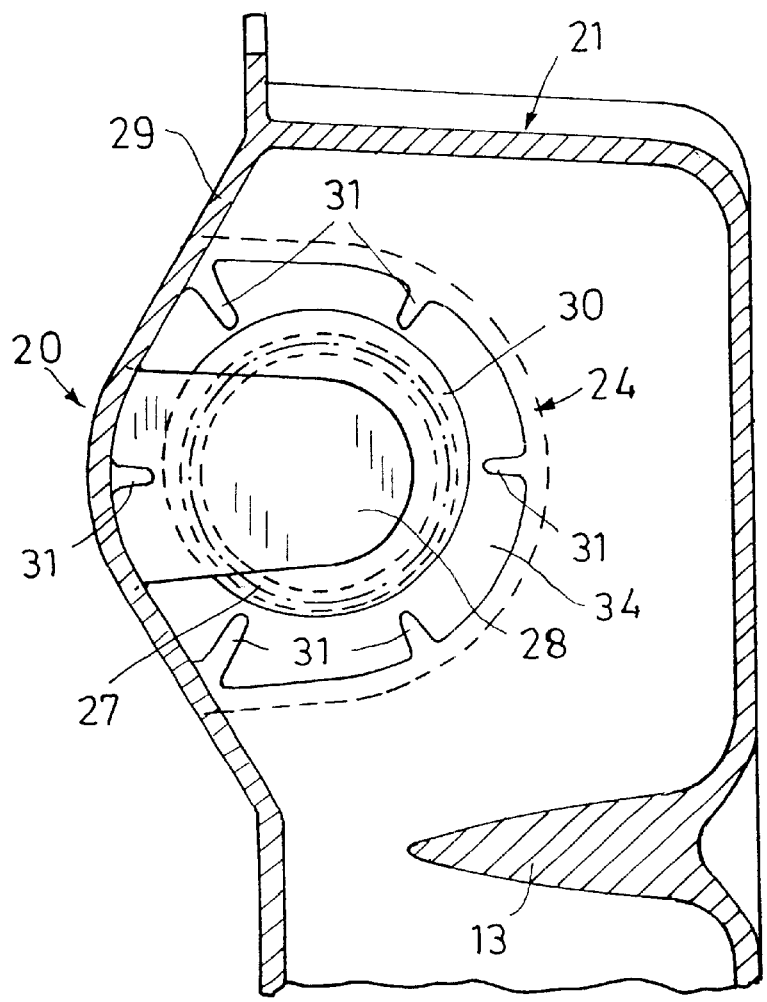
FIG. 5 shows a section along line V—V of FIG. 2.

FIG. 5 illustrates a view from below from the fine measuring chamber 11 into the valve housing 24. The radially arranged rib-shaped guide elements 31 can be seen, six of which are provided here. Said guide elements retain the valve plate 30 in such a position that they cover the valve opening encircled by the valve seat 27. In FIG. 5 the valve plate 30 is not precisely in the central position but laterally offset. In any case it completely covers the valve opening. FIG. 5 further illustrates that the bracket 28 grips below only a portion of the surface of valve plate 30. The valve plate 30 projects beyond the contour of the bracket 28 at an angle of more than 270°.

Figure 3:
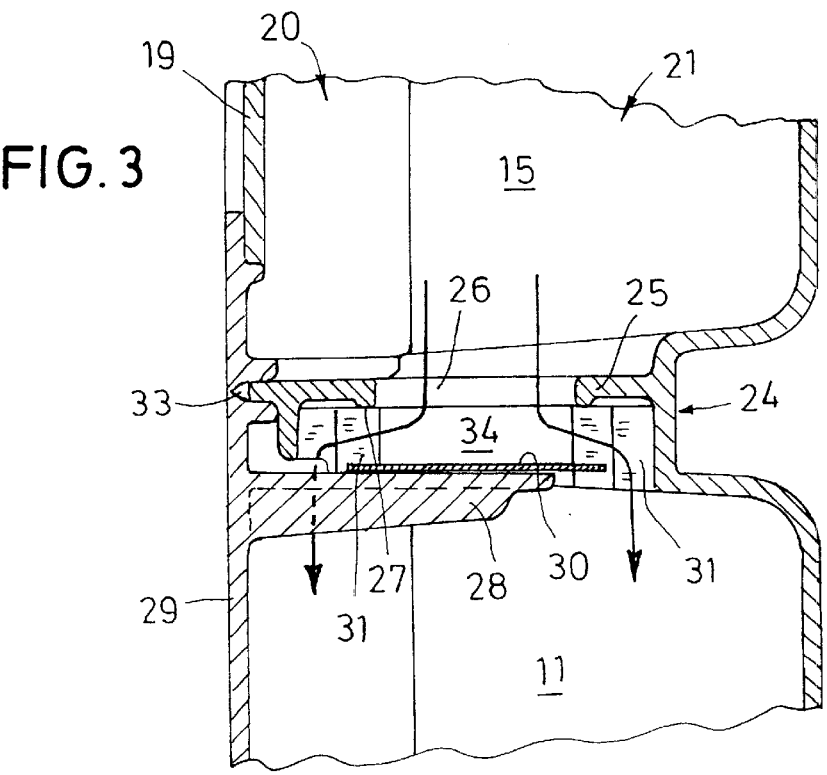
FIG. 3 shows an enlarged representation of the valve area of FIG. 2 with the valve being open in the collecting phase.

As is shown in FIG. 3 the transition wall 25, which is a component of the the rear housing part 21, extends into a groove 33 provided at the inner side of the front wall 29. All guide elements 31 are components of the rear housing part 21.

The valve chamber 34 encircled by the valve housing 24, into which the guide elements 31 radially project, has a diameter which is considerably larger than that of the valve plate 30. Therefore in the condition as shown in FIG. 3, in which the valve plate 30 rests on the bracket 28 by its weight, liquid may flow along the valve plate 30 and between the guide elements 31 into the fine measuring chamber 11.

Figure 4:
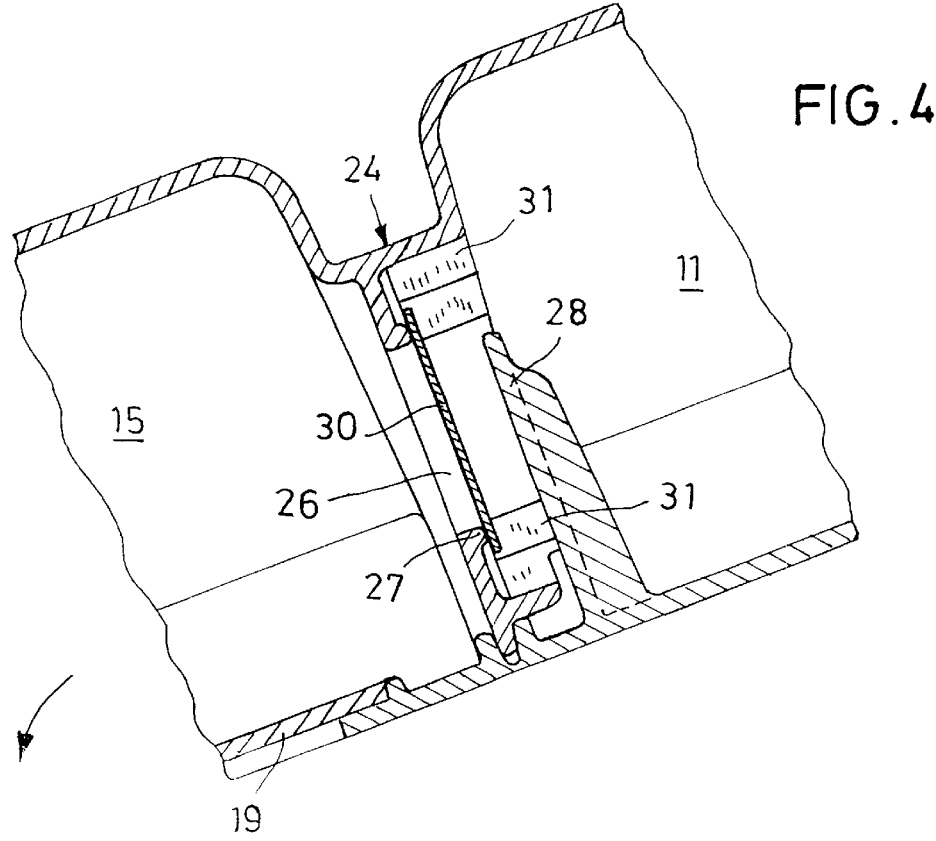
FIG. 4 shows the discharge phase in the same representation as in FIG. 2, in which the valve is closed.

If the urine measuring device is tilted to empty the measuring chambers, the liquid in the fine measuring chamber 11 presses the valve plate 30 against the valve seat 27 as illustrated in FIG. 4. This prevents liquid from refluxing from the fine measuring chamber 11 into the drip chamber 15.

What is claimed is:

1. A urine measuring device comprising a measuring device housing (20; 21) defined by two housing parts (20; 21) attached to each other with one housing part (20) forming a front part and the other housing part (21) forming a back part of the measuring device housing (20; 21) and said two housing parts (20; 21) jointly defining a drip chamber (15) having a bottom and at least one measuring chamber (11), said bottom being located between said drip chamber (15) and said at least one measuring chamber (11), said measuring device further comprising a dropper (18) leading into the drip chamber (15), an anti-reflux valve (26, 30) arranged on said bottom for preventing flow from said at least one measuring chamber (11) into said drip chamber (15), the anti-reflux valve (26, 30) including a valve opening (26) defined by a circumferential valve seat (27) located at an underside of said valve opening (26), a valve plate (30) for closing the valve opening (26), the valve plate (30) being a non-spring-biased freely movable loose part guided between lateral guide elements (31), the valve opening (26) and the guide elements (31) being components of a first one of said housing parts of said measuring device housing (20; 21), and a bracket (28) supporting the valve plate (30) being a component of a second one of said housing parts of said measuring device housing (20; 21).

2. The urine measuring device according to claim 1 wherein the lateral guide elements (31) comprising ribs projecting inwardly from a wall of a valve housing (24) between the drip chamber (15) and the at least one measuring chamber (11), and said valve housing (24) has a larger cross-section than the valve opening (26).

3. The urine measuring defined as defined in claim 2 wherein the lateral guide elements (31) are in circumferentially spaced relationship to each other and in substantially surrounding adjacent relationship to a peripheral edge of said valve plate (30).

4. The urine measuring device according to claim 1, wherein the cross-sectional area of the valve opening (26) is at least 70% larger than the inner cross-section of the dropper (18).

5. The urine measuring device as defined in claim 1 wherein the lateral guide elements (31) are in circumferentially spaced relationship to each other and in substantially surrounding adjacent relationship to a peripheral edge of said valve plate (30).

6. The urine measuring device as defined in claim 1 wherein each of said two housing parts being defined by a body wall merging with a peripheral wall terminating in a peripheral edge portion, said peripheral edge portions being disposed is substantially peripheral edge portion-to-peripheral edge portion relationship along a substantially common plane, and said valve plate supporting bracket being in spanning relationship to said common plane whereby said two housing parts, anti-reflux valve and valve plate support bracket can be readily assembled in substantially peripheral portion-to-peripheral edge relationship.

7. The urine measuring device as defined in claim 6 including cooperative first and second means of said respective first and another housing parts for accurately locating said valve plate supporting bracket relative to said circumferential valve seat.

8. The urine measuring device as defined in claim 7 including guide elements disposed on opposite sides of said common plane.

9. The urine measuring device as defined in claim 6 including guide elements disposed on opposite sides of said common plane.

10. The urine measuring device as defined in claim 6 wherein said anti-reflux valve is normally supported in an open position and lying in a plane that is substantially normal to the common plane.

11. The urine measuring device as defined in claim 1 wherein a first end of said bracket (28) is attached substantially normal to said second housing and a second end extends inwardly toward and substantially normal to said first housing.

12. The urine measuring device as defined in claim 11 wherein said bracket (28) is a single platform structure having a substantially planar top side and said second end is substantially disposed under and partially obscures said valve opening (26).

13. The urine measuring device as defined in claim 11 wherein said second end is substantially disposed under and between said valve opening (26).

\* \* \* \* \*